United States Patent [19]
Wurzburg et al.

[11] 3,961,045
[45] June 1, 1976

[54] METHOD OF TREATING ULCER
[75] Inventors: Otto B. Wurzburg, Whitehouse Station; Chester D. Szymanski, Martinsville; Leo Kruger, Kendall Park, all of N.J.
[73] Assignee: National Starch and Chemical Corporation, Bridgewater, N.J.
[22] Filed: Mar. 17, 1975
[21] Appl. No.: 558,913

Related U.S. Application Data
[62] Division of Ser. No. 408,317, Oct. 23, 1973, Pat. No. 3,893,890.

[52] U.S. Cl. .................................................. 424/78
[51] Int. Cl.² ......................................... A61K 31/74
[58] Field of Search ....................................... 424/78

[56] References Cited
FOREIGN PATENTS OR APPLICATIONS
659,211   10/1951   United Kingdom ................... 424/78

Primary Examiner—Frederick E. Waddell
Attorney, Agent, or Firm—Thomas B. Graham

[57] ABSTRACT
Water-soluble homo-and co-polymers of styrene and salts thereof having a degree of substitution from about 0.7 to about 1.3 sulfonate groups per unit of styrene are useful for treating gastric or duodenal ulcers.

1 Claim, No Drawings

METHOD OF TREATING ULCER

RELATED APPLICATIONS

This application is a division of our copending application Ser. No. 408,317 filed Oct. 23, 1973 now U.S. Pat. 3,893,890, and assigned to the assignee of the instant application.

BACKGROUND OF THE INVENTION

This invention relates to a process for inhibiting certain enzymic activity by exposing the enzyme, in an acidic-aqueous solution, to the action of a water-soluble sulfonated polymer. More particularly, this invention relates to a process for inhibiting the activity of pepsin comprising treating the pepsin with a water-soluble sulfonated polystyrene in an aqueous medium at a pH level of less than 5.0. It is due to their outstanding pepsin inhibitory ability, as exemplified hereinbelow, that the sulfonated polystyrene herein are contemplated for use as anti-ulcerogenic agents.

The term "pepsin" is intended to include all of the proteolytic enzymes of the proteinase (Endopeptidase) class of compounds which are most active at acidic pH levels (pH 1-5) and are normally capable of functioning as catalysts in the hydrolysis of proteins. These enzymes are normally found in the gastric mucosa of higher animals and are secreted in gastric juice. Pepsin is also prepared commercially from the gastric mucosa of livestock.

Although various polyelectrolytes such as amulose sulfate, amylopectin sulfate, polyvinyl sulfate and hyaluronic acid are mentioned in the literature as enzyme inhibitors, we have now found a product which is much more efficient as a pepsin inhibitor.

SUMMARY OF THE INVENTION

It is, thus, the prime object of this invention to provide a process for inhibiting pepsin activity. Another object of this invention is to provide an efficient and economical means for treating gastric and duodenal ulcers. Various objects and advantages of this invention will become apparent from the following description thereof.

We have found that the above objects are accomplished by incorporating a small amount of a homopolymer or copolymers of styrene in the acid or salt form in the acidic, aqueous reaction system having the enzyme and the substrate therein. More precisely, we have discovered that the requirements of a non-polypeptidyl polyelectrolytic pepsin inhibitor are met by utilizing water-soluble sulfonated polystyrene homo- or copolymers.

The process for inhibiting the action of pepsin according to this invention comprises exposing the active pepsin, in aqueous solution at a pH value of less than 5.0, to the action of a water-soluble sulfonated polystyrene homo- or copolymer, in acid or salt form, having a molecular weight of at least 600 and a degree of substitution (D.S.) of from about 0.7 to about 1.3 sulfonate groups per unit of styrene.

It is believed that gastric ulcers are caused primarily by the digestion of the mucosa by the pepsin of gastric juice. A decrease of this digestive activity as by pepsin inhibition would eliminate the cause of the digestive action and permit healing to take place. Pepsin can also be inactivated by increasing the pH of the gastric juice to about 5. This, however, causes the body to react by producing more acid, and the increased acid tends to nullify the effects of the pH increase. The polystyrene sulfonates being poor neutralizers would not produce this effect. Normally, if high acidity reaches the pyloric portion of the stomach further secretion of gastric juice is inhibited. The use of pH increasers (buffers) could interfere with this mechanism, while polystyrene sulfonate would decrease activity and leave intact the natural mechanisms that limit gastric juice and acid production.

DESCRIPTION OF PREFERRED EMBODIMENTS

As previously mentioned, the polyelectrolytes employed in the process of this invention are water soluble sulfonated polystyrene homopolymers and copolymers. Maleic acid, acrylic acid, and methyl styrene are suitable monomers that can be copolymerized with styrene and then sulfonated to give useful copolymers. The sulfonated derivatives of these polymers useful in the practice of this invention may have molecular weights of 600 or higher, preferably 500,000 or higher. A preferred range of molecular weight is 500,000 to 7,000,000.

As an alternate aspect of the preferred pepsin inhibitors, in accordance with this invention, salts of sulfonated polystyrene having molecular weights ranging between about 600 and about 1600 and which have been dialyzed and freeze dried, may be employed. These sulfonated derivatives of polystyrene, like the aforementioned high molecular weight salts of sulfonated polystyrene, are all characterized by their ability to display the desirable pepsin-inhibitory properties.

Among the salts of the sulfonated polystyrene which are useful in carrying out the novel process of this invention are included those having the following cations: sodium, calcium, potassium, ammonium, tetramethyl ammonium, etc.

Since pepsin is reactive at pH levels between 1.0 and about 5.0 and is deactivated above pH levels of about 5.0, and the normal pH level of gastric juice is between 1 and 3, it is not necessary that the pepsin-inhibitory polyelectrolytes be neutralized prior to utilization in the process of this invention. Therefore, in another aspect of this invention, the acid forms of the high molecular weight sulfonated polystyrenes may be utilized as pepsin-inhibitors.

It is understood that, in the selection of the pepsin-inhibitor, the degree of sulfonate group substitutions per unit of styrene and the average molecular weight are particularly significant criteria. Therefore, in the practice of this invention, it is preferred that sodium salts of sulfonated polystyrene having degrees of substitution ranging from 0.7 to 1.3 and average molecular weights between about 500,000 and 7,000,000 or higher be used.

Sulfonated polystyrenes having molecular weights of 600 to 500,000 are about as effective as sulfonated amylopectin. Certain of their physical properties, for example, low viscosity or greater solubility, may make these products superior to amylopectin sulfate as an anti-ulcerogenic compound.

With regard to the preparation of the sulfonated polystyrene and copolymers, the base polymer may be synthesized by any conventional method, e.g. bulk suspension, solution or emulsion polymerization techniques, and the sulfonating of the parent compound may be carried out according to the method taught in U.S. Pat. No. 3,072,618, using phosphorus compound-sulfur trioxide adducts.

In general, the process for inhibiting the action of pepsin according to this invention merely involves exposing the pepsin to a water-soluble sulfonated polystyrene homo- or copolymer, or salt thereof in an aqueous medium having a pH level between 1.5 and 5.0 at a temperature ranging from about 0° to about 60°C.

Obviously, the concentration of the pepsin-inhibitor used will vary depending on the nature of and molecular weight of the polymer, the intended use and the conditions therein, the normally expected rate of digestion, i.e., pepsin activity, and the extent of inhibition desired. For instance, the amount of inhibitor normally required for human use will, in most cases, vary, considerably, from that called for in other applications, e.g., non-medicative, industrial processing, veterinary treatments, etc. Therefore selection of the most effective concentration, in a given application, will be left up to the practitioner.

The pepsin-inhibitory salts of high molecular weight sulfonated polystyrene or the acid forms of said sulfonated polystyrene may be utilized, in accordance with this invention, either alone or as the primary functional ingredient in a tablet (pill) or capsule or liquid preparation such as an elixir for treatment of peptic ulcers.

In the preparation of any of the solid forms of medication, the inhibitor may be simply admixed with a conventional binder such as, for example, glucose (corn syrup), gum acacia, gelatin, starch, etc.; a disintegrator, e.g., corn starch, potato starch, methyl cellulose, agar, and the like; a lubricant, e.g., talc, magnesium stearate, sodium benzoate, leucine, etc. Suitable, optional ingredients such as diluents or bases, fluid extracts, tinctures, oils, and colorants may also be incorporated in any particular preparation.

In the preparation of anti-ulcerogenic elixers intended for oral use, for example, the pepsin-inhibitors herein can be readily stirred into the primary liquid such as an aqueous-alcoholic mixture which may also contain glycerin or sorbitol, and, at times, syrup or sweetening agents, and various other optional ingredients of the type mentioned above. A buffer can, of course, be added if an equilibrium solution pH of some value, such as 4.5. is desired for some particular reason, such as minimizing irritation of the mucous membranes of the mouth during the swallowing of the product.

Based on in vitro experiments a suitable human dosage would be 0.020 to 1.000 grams, administered orally.

The effectiveness, that is the extent of inhibition of pepsin activity by the pepsin-inhibitors embodied herein may be determined by any of the well known "assay" methods, e.g., measuring the rate of hydrolysis of a protein substrate like acid-denatured hemoglobin. Such assay methods are generally based on colorimetric or spectrophotometric measurements of the cleavage products. Standard conditions for the test are a pH level between about 1.5 and 5.0 and a temperature of 37°C. maintained over a 1/6 to 4 hour period. Usually, one unit of pepsin activity is defined as that amount of enzyme required to produce a 0.001 increase in absorbance per minute under the conditions of the assay. The widely used method developed by M. L. Anson, *Journal of Physiology*, 22, 79 (1938) using a hemoglobin substrate is a typical spectrophotometric method.

Additional information concerning conventional assay methods for pepsin activity may be obtained by referring to, inter alia, Boyle, *The Enzymes*, Vols. III and IV, Hydrolysis:Peptide Bonds, 3rd Ed. (1971).

The novel process of this invention affords several advantages. For example, it provides a simple and more efficient means for counteracting gastric or duodenal ulcers; it provides, owing to the low cost of manufacturing the sulfonated polystyrene salts, an economic means for inhibiting the action of pepsin; and because of the unique, pepsin-inhibitory properties of said salts, the process herein is readily utilizable wherever pepsin is present, e.g., the preparation of medicines for gastric disturbances, the manufacture of peptones, the digestion of gelatin in the recovery of residual silver in photographic film processing, etc. These and other advantages will become apparent from the following examples, which further illustrate but do not limit the scope of the invention.

EXAMPLE I

This example illustrates the usefulness of a water-soluble salt of a high molecular weight sulfonated polystyrene as a pepsin inhibitor and its superiority to a standard high molecular weight amylopectin sulfate.

In this case, a sulfonated polystyrene sodium salt prepared according to the method taught in Example I of U.S. Pat. No. 3,072,618, having a molecular weight of about 7,000,000 and a degree of substitution (D.S.) of 1.0, and a standard amylopectin sulfate prepared according to the method taught in assignee's U.S. Pat. No. 3,441,558, having a molecular weight of about 60,000,000 and a D.S. of 1.5, were tested for their ability to inhibit pepsin activity as set forth below.

In order to precisely estimate the extent of inhibition of pepsin activity of each of the test samples and standards, a calibration curve was first prepared. Said curve was based on the data obtained by reacting varied amounts of pepsin with a fixed amount of hemoglobin using the Anson assay method as follows:

Part I

Preparation of Calibration Curve — Eight samples containing varied amounts ranging from 0.4 to 8.0 micrograms of a thrice recrystallized commercially available pepsin, in combination with a constant amount of hemoglobin were prepared as follows:

Step 1 — The varied amount of pepsin in 1 ml. of 0.01M hydrochloric acid (pH-2.0) was placed in a 20 ml. test tube.

Step 2 — An additional 1 ml. of hydrochloric acid was added to the test tube.

Step 3 — The contents of the test tube were agitated for 20 minutes, and an aqueous solution comprising 75 mg. of a commercially available hemoglobin in 5 ml. of distilled water solution of which the pH had been adjusted to 2.0 by the addition of hydrochloric acid. These ingredients were briefly agitated, and the resulting solution was incubated for 2 hours at 37°C.

Step 4 — A suspension comprising 10 mg. of amylopectin sulfate in 1 ml. of 0.01M hydrochloric acid was added to the incubated solution to compensate for any appreciable coloration merely due to the presence of a particular inhibitor in a given test.

Step 5 — The two solutions contained in the test tube were agitated for 30 seconds, whereupon 1.0 ml. of an aqueous, 20% perchloric acid solution was added. These ingredients were briefly agitated, and the resultant solution was filtered. Then 1.0 ml. of the filtrate was added to 10.0 ml. of a 0.1M acetate buffer solution consisting of a 1:1 combination of acetic acid and sodium acetate.

The degree of pepsin activity is determined by the amount of hemoglobin digested under the standard conditions described above. The relative amount of hemoglobin digested is estimated by the optical absorbance at 275 nm (nanometers) of the material not precipitated by the perchloric acid.

The absorbance of the solution obtained in Step 5, above, was read at the prescribed wavelength of 275 nm on a Beckman DU Spectrophotometer. In each case, the actual spectrophotometric measurement was corrected by deducting 0.050, the reading obtained from a similarly prepared blank wherein the pepsin had been omitted.

The varied amounts of pepsin respectively employed in the eight samples and the corrected absorbancy readings at the prescribed wavelength were as follows:

| | Sample Identification | | | | | | | |
|---|---|---|---|---|---|---|---|---|
| | a | b | c | d | e | f | g | h |
| Amount of Pepsin | 0.4 | 0.8 | 1.0 | 1.2 | 1.6 | 2.0 | 4.0 | 8.0 |
| Absorbancy (275 nm) | 0.011 | 0.037 | 0.037 | 0.064 | 0.095 | 0.116 | 0.234 | 0.322 |

The data summarized above was used to plot the calibration curve, using the $\log_{10}$ of the varied amounts of pepsin as one coordinate and the corresponding, corrected absorbances for the other coordinate. With an allowance for very slight average deviation, particularly in the area of the extremely low concentrations of pepsin, a straight line was drawn connecting the points thus plotted in the 1.0–8 micrograms pepsin range. In the lower range of from 0 to 1.0 micrograms pepsin, the $\log_{10}$ of pepsin concentration is plotted against the $\log_{10}$ of the absorbance to give a straight line. This calibration curve showed the extent of pepsin activity normally expected, in the absence of an inhibitor, under standard conditions.

Part II

Determination of Inhibition — To determine the inhibitory properties of said sulfonated polystyrene sodium salt and said amylopectin sulfate standard, the procedural steps set forth above for the preparation of the calibration curve were repeated, except, in each case, 10 mg of the particular inhibitor dissolved in 1 ml. of 0.01M hydrochloric acid was added in Step 2, and the inhibitor in Step 4 was omitted. A control sample was also prepared by the procedure used for the calibration curve. Upon completing Step 5, the absorbancy readings, at a wavelength of 275 nm of the buffered test sample filtrate and control inhibitor were 0.064 and 0.174, respectively. These readings were then respectively corrected to 0.008 and 0.121 by subtracting the readings obtained from the corresponding blanks without pepsin. Using the aforementioned corrected absorbancy readings, reference was then made to the calibration curve to estimate the amount of pepsin activity in each sample. These values were then employed in a standard equation for determining the inhibitory property of the substance tested. Said equation was as follows:

$$\text{Per Cent Inhibition} = \left(1 - \frac{\text{Pepsin Activity with Inhibitor}}{\text{Control Pepsin Activity}}\right) \times 100$$

When the respective data obtained from the sulfonated polystyrene sodium salt and the amylopectin sulfate tests was accordingly applied to the standard equation set forth above, the per cent inhibition for the test sample was determined to be 97 and that of the standard amylopectin sulfate, 70. Thus, it becomes apparent that the ability of the sulfonated polystyrene to inhibit pepsin activity is significantly greater than that of the commercially available amylopectin sulfate inhibitor. In fact, since only 3% of the activity remains when sulfonated polystyrene was used, and 30% remains when the same amount of amylopectin sulfate is used, it is seen that polystyrene sulfonate reduces pepsin activity to 0.1 the value of the amylopectin sulfate.

EXAMPLE II

This example illustrates the effectivenss of another polystyrene sulfonate sodium salt, when employed as an inhibitor of pepsin activity according to this invention.

Part II of Example I, supra, was repeated, except 10 mg of polystyrene sulfonate sodium salt having a molecular weight of about 500,000 was used in place of the M.W. 7,000,000 sulfonated polystyrene of that example. The percent Inhibition of the test sample herein was determined to be 80.0%.

EXAMPLES III – IV

These examples illustrate the effectiveness of each of four sulfonated polystyrene salts having varied molecular weights, as pepsin inhibitors in accordance with this invention.

In each of the pepsin inhibition tests herein, Part II of Example I hereinabove was repeated, using 10 mg of a sulfonated polystyrene sodium salt having a molecular weight between 1,600 and 400,000, in 1 ml. of 0.01M hydrochloric acid. Each of the sulfonated polystyrene sodium salts tested had a D.S. of 1.0 sulfonate groups per unit of styrene. The molecular weights of said salts, their respectively corrected test and control absorbance readings, and the tests results, thus obtained, are presented in Table No. 1 below.

| Table No. 1 | | | |
|---|---|---|---|
| Example No. | Molecular Weight | Corrected Absorbances: Test and Control | Per Cent Inhibition |
| III | 400,000 | .089   .260 | 71.0 |
| IV | 70,000 | .127   .262 | 62.7 |
| V | 6,000 | .190   .329 | 61.5 |
| VI | 1,600 | .179   .343 | 69.5 |

The data summarized above clearly indicates that substantial pepsin inhibition occurred in each case.

EXAMPLE VII

This example illustrates the usefulness of a water-soluble, low molecular weight salt of sulfonated polystyrene, which had been dialyzed and freeze dried, as a pepsin inhibitor, in accordance with this invention.

In this case, the salt was a sulfonated polystyrene sodium salt having a molecular weight of about 1,600 and a D.S. of 1.0. Said salt was first dialyzed against distilled water over a four hour period and then freeze dried as set forth below.

Dialysis was carried out by placing a solution comprising 30 grams of the salt in 30 milliliters of distilled water, in a 1.625 × 20.0 inch cellophane dialysis tube. Said tube was placed in 1 gallon of distilled water for the aforesaid period. It was observed that the volume in the dialysis tube increased to about 110 milliliters. The pH of this resultant dilute solution was adjusted from 3.8 to 6.5 by the addition of a basic solution prior to freeze drying to a 4.7 gram yield of the dry, solid sulfonated polystyrene sodium salt.

When the above described salt was tested for its ability to inhibit the activity of pepsin in the manner set forth in Example I, a result of 63.8% was obtained.

EXAMPLE VIII

This example further illustrates the usefulness of a low molecular weight salt of a sulfonated polystyrene, which has been dialyzed and freeze dried, as a pepsin inhibitor, in accordance with this invention.

In this case, a sulfonated polystyrene ammonium salt having a molecular weight of about 600 and a D.S. of 1.0 was dialyzed and freeze dried in the manner utilized in Example VII hereinabove. Upon completion of the four dialysis period, the volume in the dialysis tube was found to have increased to about 200 milliliters. The pH of this solution was adjusted from 4.8 to 6.5 by the addition of a basic solution, and said solution was freeze dried to a salt product yield of 16 grams. When a sample of the recovered salt was tested for its ability to inhibit pepsin activity, a result of approximately 73.9 percent inhibition was obtained.

EXAMPLE IX

This example illustrates the usefulness of a sulfonated polystyrene ammonium salt, having a slightly higher D.S. and a considerably higher molecular weight than that employed in Example VIII hereinabove, as a pepsin inhibitor in accordance with this invention.

In this case, a commercially available sulfonated polystyrene ammonium salt having a D.S. of 1.2 and a molecular weight of about 10,000 was tested for its pepsin inhibitory property by the method utilized in Example I. A test result of approximately 65 percent inhibition was obtained.

EXAMPLE X

This example illustrates the usefulness of a sulfonated copolymer of styrene and another monomer. A copolymer of 70% styrene/30% methyl methacrylate was sulfonated to a D.S. of about 0.7 with respect to monomers present. Its molecular weight was about 400,000. The % inhibition was determined by the procedure of Example I, and found to be 51%. This is somewhat lower than the 70% found for the amylopectin sulfate standard but may be useful if the physical properties are such as to give better compatibility with other ingredients, or longer retention in the stomach.

Summarizing, it is seen that this invention provides a novel process for inhibiting the activity of pepsin.

Variations may be made in the procedures and proportions without departing from the scope of this invention as defined by the following claims.

What is claimed is:

1. A method for treating gastric or duodenal ulcers in humans in need of such treatment comprising administering orally thereto an effective amount within the range of from 0.020 to 1.000 grams of a water-soluble polymer selected from the group consisting of sulfonated homo- and copolymers of styrene and salts thereof having a degree of substitution from about 0.7 to about 1.3 sulfonate groups per unit of styrene and an average molecular weight within the range of 600 to 7,000,000.

* * * * *